(12) United States Patent
Fenton

(10) Patent No.: US 6,869,422 B2
(45) Date of Patent: Mar. 22, 2005

(54) OSTOMY POUCH AND METHOD OF ASSEMBLY

(75) Inventor: Gary H. Fenton, Bedford, OH (US)

(73) Assignee: Marlen Manufacturing & Development Co., Ltd., Bedford, OH (US)

( * ) Notice: Subject to any disclaimer, the term of this patent is extended or adjusted under 35 U.S.C. 154(b) by 0 days.

(21) Appl. No.: 10/870,132

(22) Filed: Jun. 17, 2004

(65) Prior Publication Data

US 2004/0230170 A1 Nov. 18, 2004

Related U.S. Application Data

(62) Division of application No. 09/758,726, filed on Jan. 11, 2001, now Pat. No. 6,790,200.

(51) Int. Cl.[7] .................................................. A61F 5/44
(52) U.S. Cl. ........................................ 604/338; 604/332
(58) Field of Search .................................. 604/332–344, 604/322

(56) References Cited

U.S. PATENT DOCUMENTS

| | | | | |
|---|---|---|---|---|
| 2,818,069 A | * | 12/1957 | Fenton | 604/338 |
| 3,283,757 A | * | 11/1966 | Nelson | 604/334 |
| 3,295,145 A | * | 1/1967 | Ericson | 4/144.3 |
| 4,387,713 A | * | 6/1983 | Calanni | 604/333 |
| 4,561,858 A | * | 12/1985 | Allen et al. | 604/336 |
| 4,834,731 A | | 5/1989 | Nowak et al. | |
| 4,973,323 A | * | 11/1990 | Kaczmarek et al. | 604/339 |
| 5,000,748 A | * | 3/1991 | Fenton | 604/340 |
| 5,004,464 A | * | 4/1991 | Leise, Jr. | 604/338 |
| 5,015,244 A | * | 5/1991 | Cross | 604/344 |
| 5,330,454 A | * | 7/1994 | Klingler et al. | 604/338 |
| 5,429,626 A | | 7/1995 | Fenton | |
| 5,618,276 A | | 4/1997 | Leise et al. | |
| 6,790,200 B2 | * | 9/2004 | Fenton | 604/338 |

* cited by examiner

Primary Examiner—Larry I. Schwartz
Assistant Examiner—Michele Kidwell
(74) Attorney, Agent, or Firm—Pearne & Gordon LLP

(57) ABSTRACT

An ostomy appliance and a mounting disc include an ostomy pouch having a stoma receiving portal. The mounting disc is sealed about the portal and includes a flexible plastic disc having a convex central body portion and a surrounding annular rim. A first foam disc having an outer diameter corresponding to the outer diameter of the rim is adhesively adhered to the plastic disc. A second foam disc is adhered to an adhesive face of the first foam disc and has an outer diameter greater than the plastic disc. A hydrocolloid skin shield disc having an outer diameter corresponding to the outer diameter of the second foam disc is adhesively adhered to an adhesive face of the second disc.

10 Claims, 3 Drawing Sheets

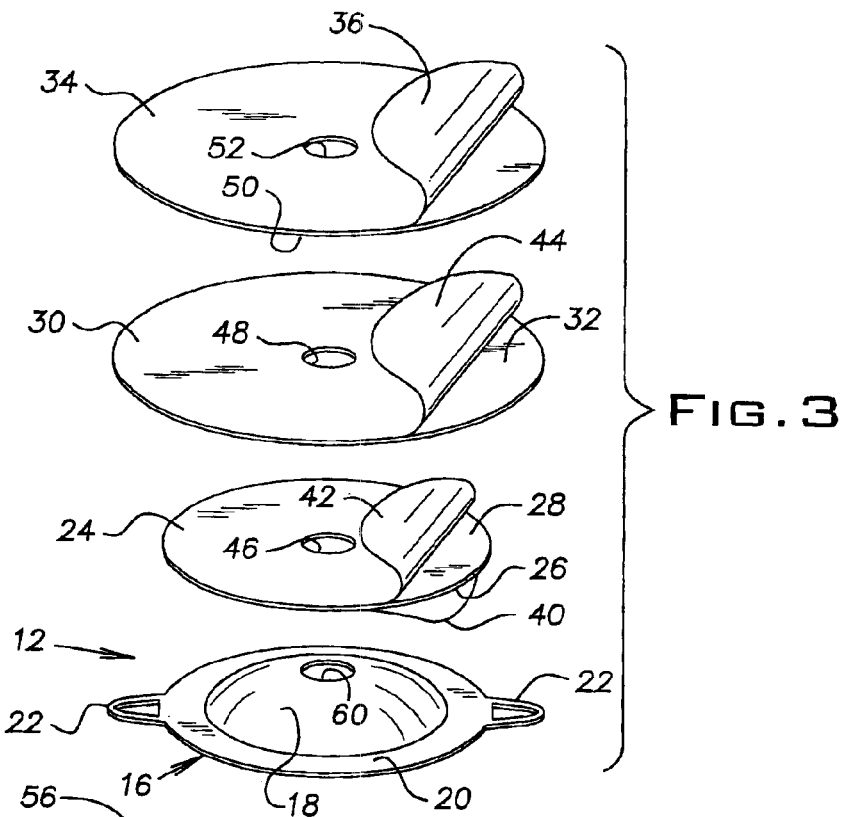
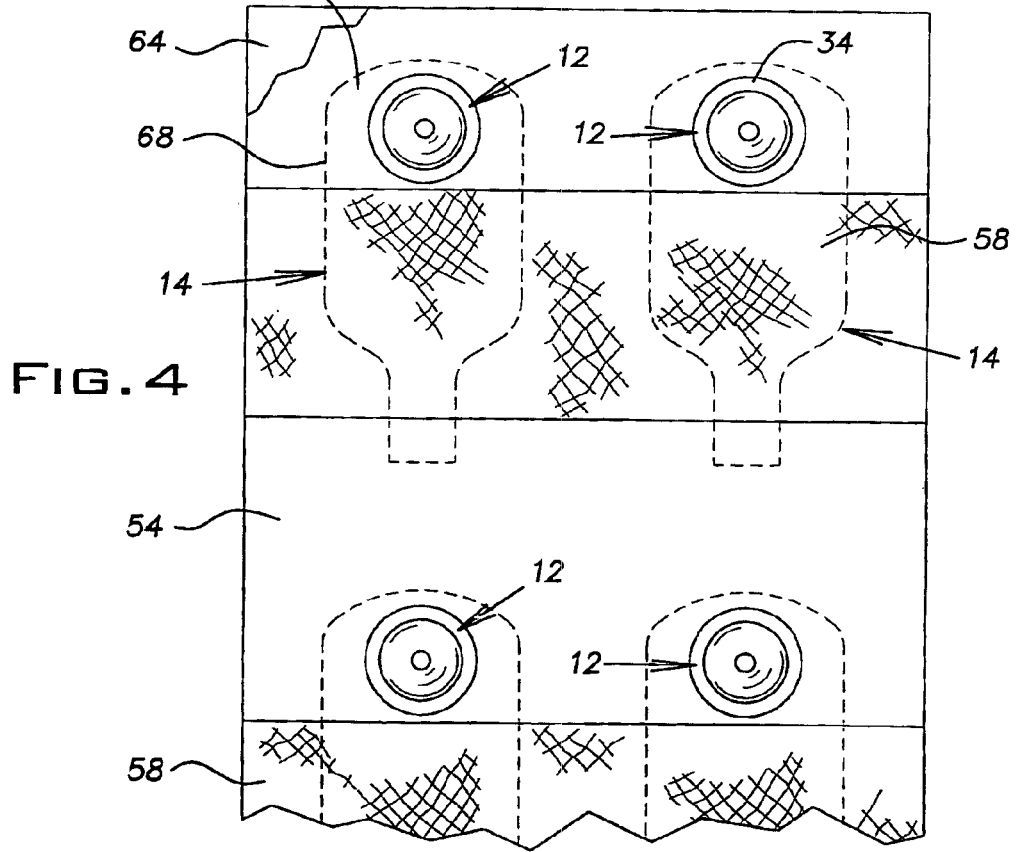

OSTOMY POUCH AND METHOD OF ASSEMBLY

This application is a divisional of U.S. application Ser. No. 09/758,726, filed Jan. 11, 2001, now U.S. Pat. No. 6,790,200.

BACKGROUND OF THE INVENTION

This invention relates to a method of assembling an ostomy pouch and, more particularly, to a method of assembling a mounting plate for an ostomy pouch and for attracting the plate to a plastic sheet which forms one side of an ostomy pouch.

Typical one-piece ostomy appliances include a mounting faceplate interposed between a convex disc and an ostomy pouch. The proximal convex face of the disc is covered with a hydrocolloid skin barrier to seal against the periostomal skin surfaces of the ostomate. The distal wall of the faceplate is secured to a proximal wall of the pouch about a stoma opening in the pouch either by an adhesive, ultrasonic sealing, or heat sealing. The proximal wall of the faceplate is adhered to the distal face of the convex disc by an adhesive. The faceplate extends beyond the periphery of the convex disc so that the adhesive coating on the proximal wall of the faceplate is adhered to the ostomate's skin to mount the ostomy appliance.

Even though the mounting adhesive is hypoallergenic, medical grade, pressure-sensitive adhesive that is permeable to gas and water vapor, many ostomates find that the repeated removal of adhesive faceplates is quite painful, and, in some cases, causes skin ulceration. Those ostomates prefer the appliance to be belt-mounted with only the hydrocolloid skin barrier in contact with the periostomal skin areas.

SUMMARY OF THE INVENTION

This invention provides an ostomy appliance which overcomes many of the prior art problems and provides a simplified technique for making the appliance.

A method of assembly includes the steps of providing a flexible plastic disc having a convex central body portion and a surrounding annular rim. A first foam disc is provided. The disc has first and second faces coated with a pressure-sensitive adhesive and an outer diameter substantially corresponding to the outer diameter of the plastic disc. A second foam disc having a pressure-sensitive adhesive coating on one of its faces and having an outer diameter greater than the outer diameter of the plastic disc is provided. The other uncoated face of the second foam disc is adhered to the first foam disc. An adhesive hydrocolloid skin barrier disc having an outer diameter corresponding to that of the second foam disc is adhered to the adhesive face of the second disc. The second face of the first foam disc is adhered to the plastic disc. Heat and pressure are applied to the hydrocolloid disc in an annular zone surrounding the convex body portion of the plastic disc to seal the first and second foam disc assembly to the plastic disc, to mold the hydrocolloid disc to the shape of the convex body portion, and to form a mounting disc.

At least one mounting disc is placed on a plastic sheet which will form the proximal wall of one or more ostomy pouches. The proximal surface of the sheet may be covered with a cloth-like porous material for the comfort of the wearer. The center of each disc is die-cut to provide a stoma-receiving opening. The sheet is provided with apertures having diameters generally coinciding with the inside diameter of the annular rim of the convex disc.

With a mounting disc positioned so that the annular rim of the convex disc contacts an annular zone of the sheet surrounding the aperture, heat is applied to the disc to fuse the sheet thereto. Thereafter, the sheet and its attached mounting discs are placed on another sheet which will form the distal wall of the ostomy pouch or pouches. Each pouch is then die-cut to shape and the pouch perimeter is heat-sealed.

BRIEF DESCRIPTION OF THE DRAWINGS

FIG. 3 is an exploded view of a mounting disc according to this invention; and

FIG. 4 is a plan view of the mounting discs applied to a plastic sheet.

DETAILED DESCRIPTION OF THE INVENTION

Figure 1:
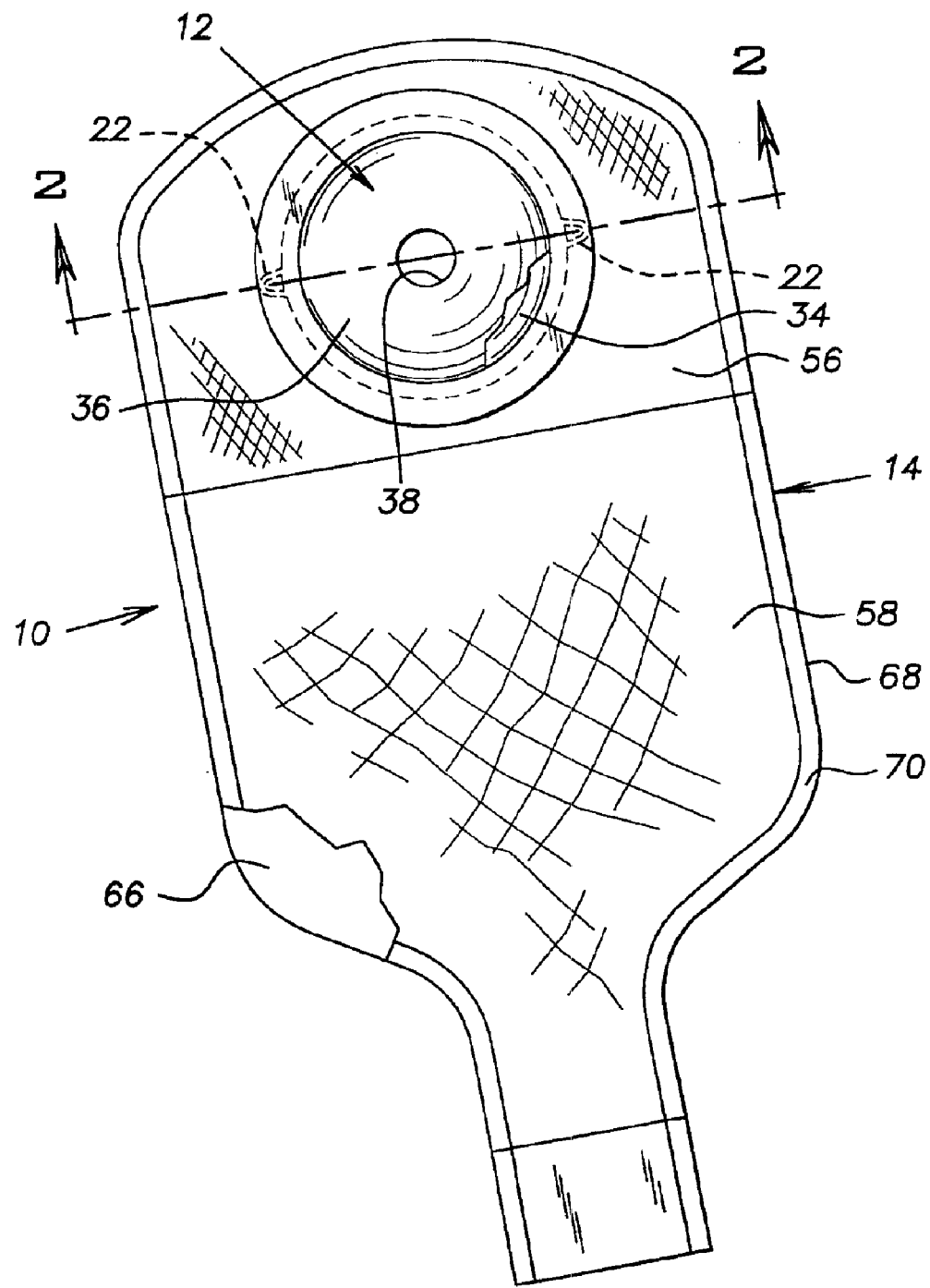
FIG. 1 is a proximal elevational view of an ostomy appliance according to this invention.
Figure 2:
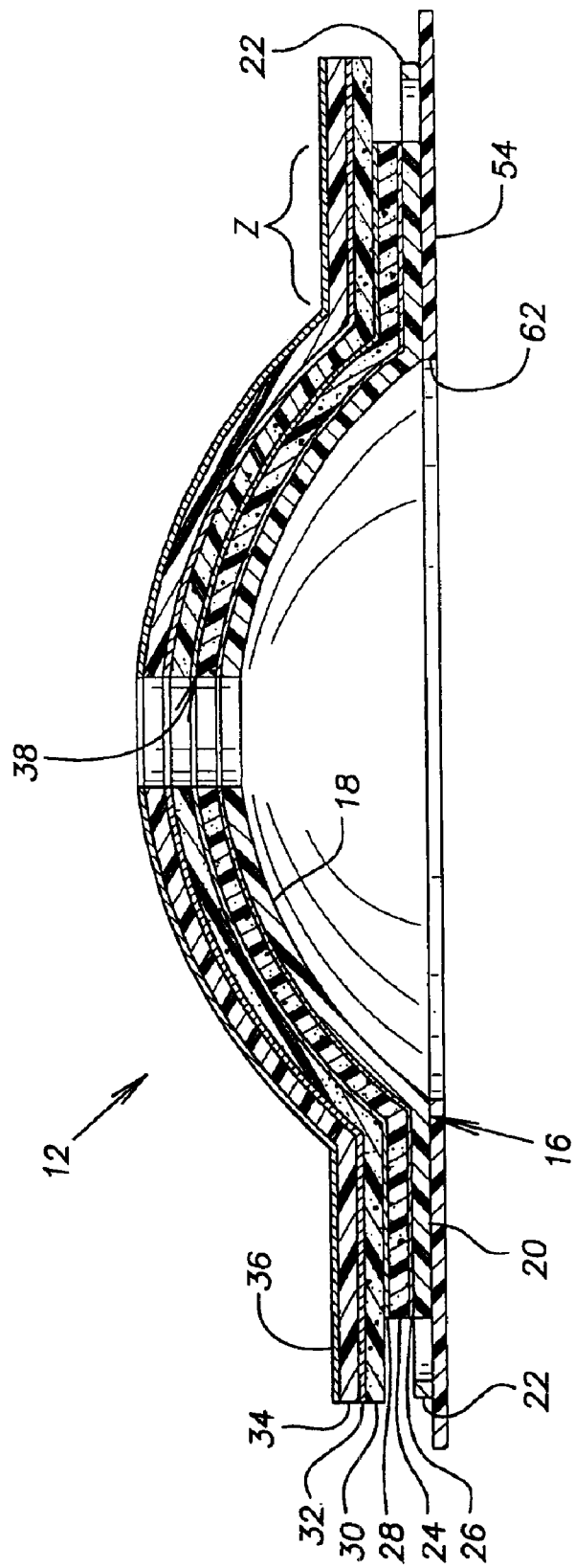
FIG. 2 is a cross-sectional view, the plane of the section being indicated by the line 2—2 in FIG. 1.

Referring now to the drawings, and particularly to FIGS. 1–3, there is illustrated an ostomy appliance assembly 10 according to this invention. The assembly 10 includes a mounting disc 12, adapted to be attached to a fastening belt (not shown) of an ostomate, and an ostomy pouch 14.

The mounting disc 12 includes a flexible plastic disc 16 having a convex central body portion 18 and a surrounding annular rim 20. The disc may be molded from a copolymer of ethylene and vinyl acetate (EVA). The EVA copolymer may be "ELVAX"® 450, produced by E.I. DuPont de Nemours, Inc., Wilmington, Del. The disc 16 is provided with diametrically opposed and radially extending belt mounting loops 22 at its periphery.

A first soft resilient thermoplastic foam disc 24 covers the flexible plastic disc 16. The foam disc 24 has pressure-sensitive adhesive layers 26 and 28 on each of its faces and one face is attached to the plastic disc 16. The foam disc 24, when applied to the disc 16, has an outer diameter substantially corresponding to the outer diameter of the disc 16.

A second soft, resilient thermoplastic foam disc 30 covers the first foam disc 24. The foam disc 30 has a pressure-sensitive adhesive layer 32 on one face, and the other face of the disc 24 is adhesively attached to the adhesive layer 28 of the first foam disc 24 so that the pressure-sensitive layer is exposed. The foam disc 30 has an outer diameter greater than the outer diameters of the first foam disc 24 and the disc 16. The belt mounting loops 22 do not extend beyond the diameter of the second foam disc 30 so that the skin of the ostomate is protected from belt hooks passing through the belt mounting loops 22.

An adhesive hydrocolloid skin barrier disc 34 having an outer diameter corresponding to that of the second foam disc 30 is placed on the adhesive layer 32 of the second foam disc 30. Preferably the exposed surface of the disc 34 is covered by a thin release film 36 which is removed just prior to use. Heat and pressure are applied to an annular zone z (FIG. 2) to seal the discs and to smooth the foam and hydrocolloid discs over the convex central body portion 18 of the plastic disc 16.

The adhesive skin barrier disc 34 is pliable and has both dry and wet tack. Suitable materials are Karaya-glycerine formulations or mixtures of polyacrylamide resins and other polyols and mixtures of elastomers and hydrocolloids. A stoma inlet portal 38 is provided at the center of the assembly, as illustrated in FIG. 2.

The first and second foam discs 24 and 30, the hydrocolloid skin barrier disc 34, and the plastic disc 16 are assembled in the following manner. For ease of handling during the assembly operation, the pressure-sensitive adhesive layers 26 and 28 of the first foam disc 24 are respectively covered by protective liners 40 and 42, and the adhesive layer 32 of the foam disc 30 is covered by a protective liner 44. The release liner 42 is stripped from the adhesive layer 28 and the disc 24 is adhered concentrically to the foam disc 30. To aid in this operation, pilot apertures 46 and 48 are respectively provided at the centers of the discs 24 and 30.

After the discs 24 and 30 are assembled, the liner 44 is stripped from the adhesive layer 32 of the disc 30 and the adhesive layer 32 of the disc 30 is applied concentrically to one face 50 of the adhesive hydrocolloid skin barrier disc 34. To aid in this operation, a pilot aperture 52 is provide at the center of the adhesive hydrocolloid skin barrier disc 34.

After the discs 24, 30 and 34 are assembled, the liner 40 is stripped from the adhesive layer 26 of the disc 24 and the adhesive layer of the disc 24 is applied concentrically to the convex face of the plastic disc 16. To aid in this operation, a pilot aperture 60 is provided at the center of the disc 16.

After heat and pressure is applied at the zone z, as was previously described, at least one mounting disc 12 is placed on a plastic sheet 54 (FIG. 4) which will form the proximal wall 56 of one or more ostomy pouches 14. Each disc 12 is placed over an opening 62 (FIG. 2) in the sheet 54. The proximal surface of the sheet 54 may be covered with a cloth-like porous material 58 for the comfort of the wearer. The pilot openings 52, 48, 46, and 60 may be die-cut to form the properly sized stoma inlet portal 38. Heat and pressure are again applied at the zone z to seal the annular rim 20 to the sheet 54. After the sealing operation, the sheet 54 is backed by another sheet 64 which will form a distal wall 66 of one or more ostomy pouches 14. The pouches 14 are then formed by die-cutting along a line 68 and heat sealing along a peripheral band 70 (FIG. 1).

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. A method of assembling a mounting disc for an ostomy appliance comprising the steps of providing a flexible plastic disc having a convex central body portion and a surrounding annular rim, providing a first foam disc having first and second faces and having pressure-sensitive adhesive on each of said faces covered by first and second release liners, said first foam disc having an outer diameter substantially corresponding to the outer diameter of said flexible plastic disc, providing a second foam disc having first and second faces and having pressure-sensitive adhesive on said first face of said second foam disc covered by a third release liner, said second foam disc having an outer diameter greater than the outer diameter of said flexible plastic disc, providing an adhesive skin barrier disc having an outer diameter substantially corresponding to the outer diameter of said second foam disc, removing said first liner from the adhesive on the first face of said first disc and adhering said first face to the second face of said second foam disc, removing the third release liner from the adhesive on the first face of said second foam disc and adhering the first face of the second foam disc to one face of the adhesive skin barrier disc, removing said second liner from the adhesive on the second face of said first disc and adhering said second face to the convex central body portion and the surrounding annular rim of said plastic disc, applying heat and pressure to said skin barrier disc at an annular zone corresponding to said annular rim to seal said discs and to smooth the foam and hydrocolloid discs over the central body portion of the plastic disc.

2. A method according to claim 1 including the step of providing diametrically opposed and radially extending mounting loops at a periphery of said flexible plastic disc.

3. A method according to claim 2 wherein said mounting loops do not extend beyond the diameter of said skin barrier disc and said second foam disc.

4. A method according to claim 1 wherein said skin barrier disc is an elastomer hydrocolloid mixture.

5. A method according to claim 1 including the step of covering another face of said skin barrier disc with a removable protective skin.

6. A method of assembling an ostomy pouch comprising the steps of providing a flexible plastic disc having a convex central body portion and a surrounding annular rim, providing a first foam disc having first and second faces and having pressure-sensitive adhesive on each of said faces covered by first and second release liners, said first foam disc having an outer diameter substantially corresponding to the outer diameter of said flexible plastic disc, providing a second foam disc having first and second faces and having pressure-sensitive adhesive on said first face of said second foam disc covered by a third release liner, said second foam disc having an outer diameter greater than the outer diameter of said flexible plastic disc, providing an adhesive skin barrier disc having an outer diameter substantially corresponding to the outer diameter of said second foam disc, removing said first liner from the adhesive on the first face of said first disc and adhering said first face to the second face of said second foam disc, removing the third release liner from the adhesive on the first face of said second foam disc and adhering the first face of the second foam disc to one face of the adhesive skin barrier disc, removing said second liner from the adhesive on the second face of said first disc and adhering said second face to the convex central body portion and the surrounding annular rim of said plastic disc, applying heat and pressure to said skin barrier disc at an annular zone corresponding to said annular rim to seal said discs and to smooth the foam and hydrocolloid discs over the central body portion of the plastic disc, and to provide a mounting disc, providing a first sheet of thin plastic material, cutting at least one circular opening in said sheet having a diameter substantially corresponding to an inside diameter of said annular rim, placing said annular rim on an opening in said sheet, sealing said annular rim to said sheet, placing said first sheet on a second sheet of thin plastic material, cutting said sheets to a desired pouch shape and sealing a perimeter of said pouch.

7. A method according to claim 6 including the step of providing diametrically opposed and radially extending mounting loops at a periphery of said flexible plastic disc.

8. A method according to claim 6 wherein said mounting loops do not extend beyond the diameter of said skin barrier disc and said second foam disc.

9. A method according to claim 6 wherein said skin barrier disc is an elastomer hydrocolloid mixture.

10. A method according to claim 6 including the step of covering another face of said skin barrier disc with a removable protective skin.

* * * * *